(12) United States Patent
Cuello et al.

(10) Patent No.: US 10,829,725 B2
(45) Date of Patent: Nov. 10, 2020

(54) AIR ACCORDION BIOREACTOR

(71) Applicant: The Arizona Board of Regents on Behalf of the University of Arizona, Tucson, AZ (US)

(72) Inventors: Joel L. Cuello, Tucson, AZ (US); Sara S. Kuwahara, Tucson, AZ (US); Takanori Hoshino, Kanagawa (JP); Cody L. Brown, Tucson, AZ (US)

(73) Assignee: The Arizona Board of Regents on behalf of The University of Arizona, Tucson, AZ (US)

( * ) Notice: Subject to any disclaimer, the term of this patent is extended or adjusted under 35 U.S.C. 154(b) by 186 days.

(21) Appl. No.: 15/115,458

(22) PCT Filed: Jan. 30, 2015

(86) PCT No.: PCT/US2015/013836
§ 371 (c)(1),
(2) Date: Jul. 29, 2016

(87) PCT Pub. No.: WO2015/116963
PCT Pub. Date: Aug. 6, 2015

(65) Prior Publication Data
US 2017/0166849 A1  Jun. 15, 2017

Related U.S. Application Data

(60) Provisional application No. 61/934,748, filed on Feb. 1, 2014.

(51) Int. Cl.
*C12M 3/00* (2006.01)
*C12M 1/00* (2006.01)
(Continued)

(52) U.S. Cl.
CPC ............ *C12M 21/02* (2013.01); *C12M 21/12* (2013.01); *C12M 23/22* (2013.01); *C12M 23/26* (2013.01);
(Continued)

(58) Field of Classification Search
CPC ...... C12M 21/02; C12M 23/14; C12M 23/26; C12M 29/06; C12M 29/24
See application file for complete search history.

(56) References Cited

U.S. PATENT DOCUMENTS

| 4,952,511 A | 8/1990 | Radmer |
| 5,162,051 A | 11/1992 | Hoeksema |

(Continued)

FOREIGN PATENT DOCUMENTS

| GB | 2330589 | 4/1999 |
| WO | WO 95/06111 | 3/1995 |

(Continued)

OTHER PUBLICATIONS

"Algae Photobioreactor in UA: UA Researcher Predicts Algae Biofuel at the Pump in 5 Years," http://home.ateneoinnovation.org/index.php?option=com_content&view=article&id=449:algae-photobioreactor-in-ua&catid=1:latest-news&Itemid=50, 5 pages, Feb. 22, 2010.

(Continued)

*Primary Examiner* — Nathan A Bowers
(74) *Attorney, Agent, or Firm* — Klarquist Sparkman, LLP

(57) ABSTRACT

Disclosed herein are bioreactors that include a container for holding fluid aligned on a vertical axis, wherein at least a portion of the container is oriented at an angle relative to the vertical axis, wherein the angle is from about 0° to 90°. In some embodiments, the container is placed on a support structure with portions of the container oriented at alternat- (Continued)

ing angles. The system is essentially closed except for at least one opening (for example an opening at the bottom edge) that allows for the introduction of gases and/or nutrients. The gas and/or nutrients are introduced in such a way as to provide mixing and aeration of a cell culture in the bioreactor. Also disclosed are methods of culturing cells (such as microalgae, macroalgae, bacteria, fungi, insect cells, plant cells, animal cells, or plant or animal tissue or organs) using a bioreactor described herein.

13 Claims, 6 Drawing Sheets

(51) Int. Cl.
C12M 1/02 (2006.01)
C12M 1/34 (2006.01)

(52) U.S. Cl.
CPC ............ C12M 23/44 (2013.01); C12M 23/58 (2013.01); C12M 29/06 (2013.01); C12M 31/02 (2013.01); C12M 41/18 (2013.01); C12M 41/26 (2013.01); C12M 41/34 (2013.01); C12M 41/36 (2013.01)

(56) References Cited

U.S. PATENT DOCUMENTS

| | | | |
|---|---|---|---|
| 5,443,985 A | 8/1995 | Lu et al. | |
| 5,846,816 A * | 12/1998 | Forth | C12M 21/02 435/292.1 |
| 6,509,188 B1 | 1/2003 | Trosch et al. | |
| 2008/0160591 A1 | 7/2008 | Willson et al. | |
| 2008/0274494 A1 | 11/2008 | Kertz | |
| 2009/0011492 A1* | 1/2009 | Berzin | B01D 53/84 435/257.1 |
| 2009/0053762 A1 | 2/2009 | Shaaltiel | |
| 2011/0165666 A1* | 7/2011 | Dahle | C12M 21/02 435/292.1 |
| 2011/0287541 A1 | 11/2011 | Cuello et al. | |
| 2017/0320027 A1* | 11/2017 | Morrissey | B01F 7/00241 |

FOREIGN PATENT DOCUMENTS

| | | |
|---|---|---|
| WO | WO 2007/098150 | 8/2007 |
| WO | WO 2009/040383 | 4/2009 |
| WO | WO 2009/069967 | 6/2009 |
| WO | WO 2009/090549 | 7/2009 |
| WO | WO 2010/076795 | 7/2010 |
| WO | WO 2011/099016 | 8/2011 |
| WO | WO 2013/082713 | 6/2013 |

OTHER PUBLICATIONS

Xu et al., "Microalgal bioreactors: Challenges and opportunities," *Eng. Life Sci.*, vol. 9, No. 3, pp. 178-189, 2009.

* cited by examiner

FIG. 3A
FIG. 3B
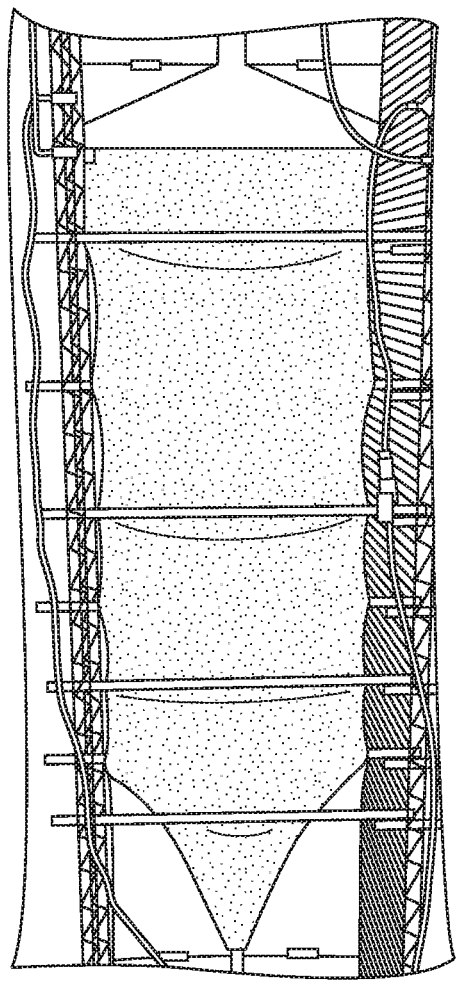
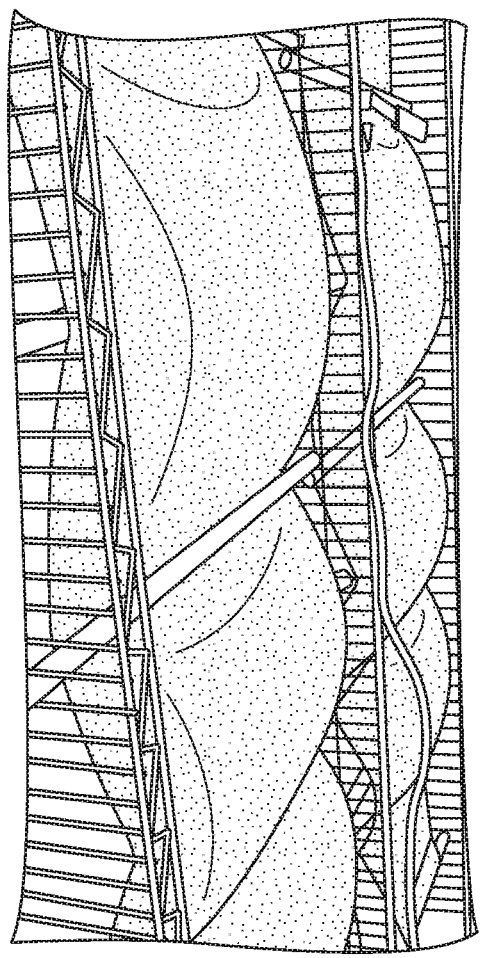

AIR ACCORDION BIOREACTOR

CROSS REFERENCE TO RELATED APPLICATION

This is the § 371 U.S. National Stage of International Application No. PCT/US2015/013836, filed Jan. 30, 2015, which was published in English under PCT Article 21(2), which in turn claims the benefit of U.S. Provisional Application No. 61/934,748, filed Feb. 1, 2014, which is herein incorporated by reference in its entirety.

FIELD

This disclosure relates to bioreactors, particularly photobioreactors, and methods of their use, for example for cell culture.

PARTIES TO JOINT RESEARCH AGREEMENT

This application describes and claims certain subject matter that was developed under a written joint research agreement between The Arizona Board of Regents on behalf of the University of Arizona and Biopharmia AS.

BACKGROUND

Commercial large-scale production of microalgae began in the late 1960s in Japan, then spread throughout the world in the 1970s and 1980s. In recent years the number of commercial large-scale facilities around the world has increased at a nearly exponential rate as demand for animal feed, nutraceuticals, vitamins and lipids, biofuels, and bioplastics has increased. As natural resources become increasingly scarce it is evident that the need for large-scale commercial production of microalgae and other cell types will also grow.

SUMMARY

Disclosed herein are bioreactors (such as photobioreactors, for example for algal culture) that have the advantages of closed systems and also are relatively low cost to construct and operate. The disclosed bioreactors are modular, allowing for simple scale-up, and can be easily adjusted (for example, automatically) for optimizing culture conditions, such as incident light exposure.

Disclosed herein are bioreactors that include a container for holding fluid aligned on a vertical axis, wherein at least a portion of the container is oriented at an angle relative to the vertical axis, wherein the angle is from about 0° to 90°. In some embodiments, the container is placed on a support structure with portions of the container oriented at alternating angles, such that the configuration suggests an accordion. The system is essentially closed except for at least one opening (for example an opening at the bottom edge) that allows for the introduction of gases and/or nutrients. The system may also include one or more additional openings or ports (for example in a side edge of the bioreactor or in the first or second sheet) for air venting, adding or removing cell culture medium and/or cells, or sensor placement. Gas and/or nutrients are introduced through an opening in such a way as to provide mixing and aeration of a cell culture in the bioreactor. In some examples, a gas sparging device is attached to an opening in the bottom edge, for example directly or with a tube.

The disclosure includes embodiments including a modular arrangement of the disclosed bioreactors, such as multiple series of bioreactors arranged adjacent to one another. In some examples, the modular arrangement includes at least one common structural support (such as at least one horizontal support) that supports the multiple bioreactors.

The disclosure also includes methods of culturing cells including incubating a suspension of cells in a disclosed bioreactor. In some examples, the cells include microalgae, macroalgae, bacteria, fungi, insect cells, plant cells, animal cells (such as mammalian cells), or plant or animal tissue or organs. In particular examples, the method includes exposing the culture in the bioreactor to a light source (such as sunlight or an artificial light source).

The foregoing and other features of the disclosure will become more apparent from the following detailed description, which proceeds with reference to the accompanying figures.

BRIEF DESCRIPTION OF THE DRAWINGS

FIGS. 3A and 3B are digital images of front (FIG. 3A) and side (FIG. 3B) views of exemplary Air Accordion bioreactors in operation.

DETAILED DESCRIPTION

Figure 1:
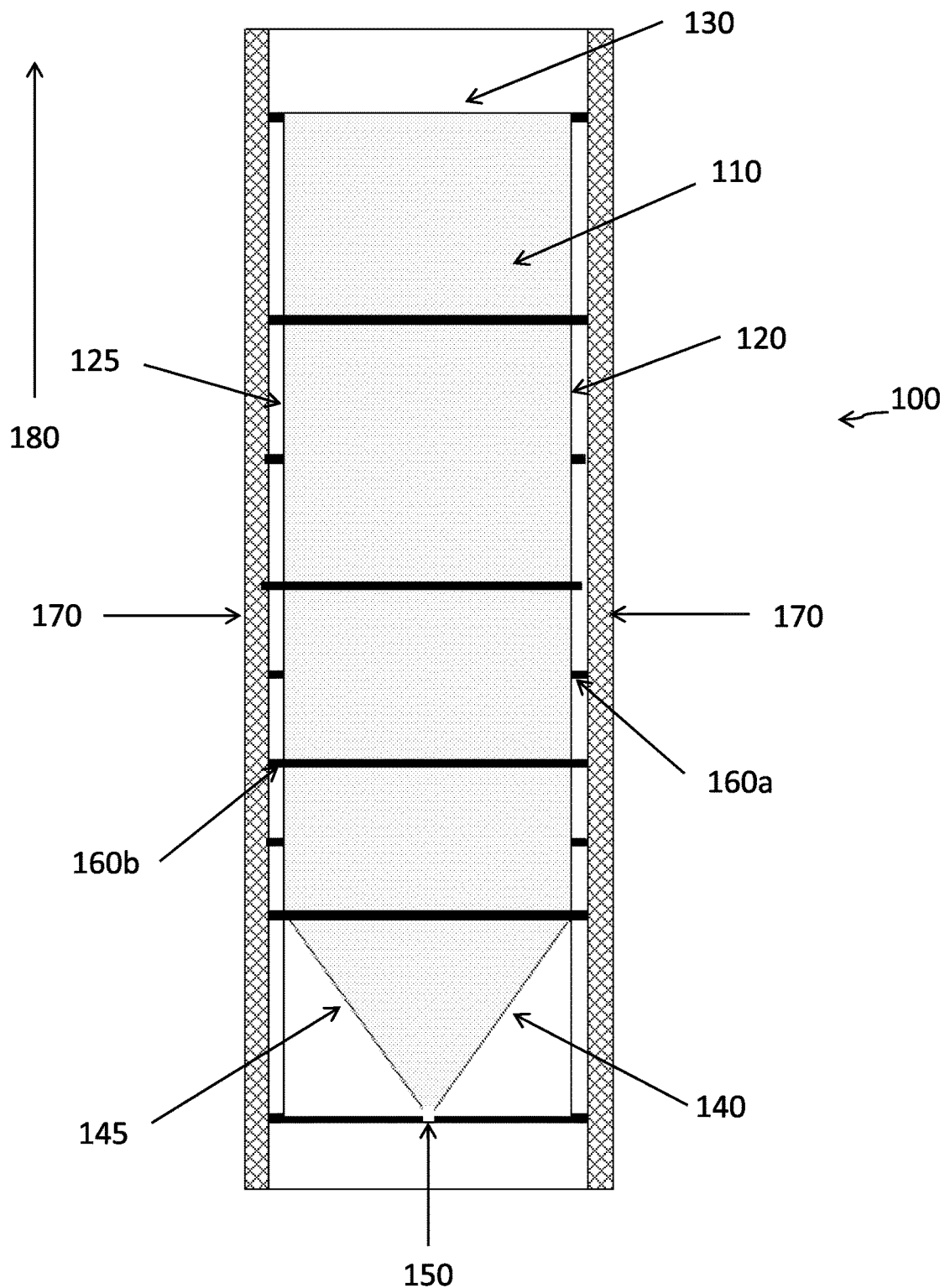
FIG. 1 is a flattened elevation view of an exemplary bioreactor of the disclosure.

The bioreactor systems disclosed herein (referred to in some examples herein as an "Air Accordion" bioreactor) provide highly efficient biomass production in a closed system with advantages of reduced costs for construction and operation (for example, low cost materials and reduced energy and water requirements), simplicity, modularity, and flexibility.

Although bioreactors and methods are described herein primarily with respect to algae culture (for example, the culture of microalgae), the disclosed bioreactors and methods in their several embodiments are also suitable for culture of other photosynthetic cells, including for example, cyanobacteria. In other examples, the bioreactors and methods are also suitable for culture of other cells and/or organisms, such as fungi, bacteria, viruses (such as algae, plant, bacterial, or fungal viruses), plant cells or plant tissue, and/or mammalian cells or tissue.

Unless otherwise explained, all technical and scientific terms used herein have the same meaning as commonly understood by one of ordinary skill in the art to which this disclosure belongs. The singular terms "a," "an," and "the" include plural referents unless the context clearly indicates otherwise. Similarly, the word "or" is intended to include "and" unless the context clearly indicates otherwise. Although methods and materials similar or equivalent to those described herein can be used in the practice or testing of this disclosure, suitable methods and materials are described below. The term "comprises" means "includes." All publications, patent applications, patents, and other references mentioned herein are incorporated by reference in their entirety for all purposes. In case of conflict, the present specification, including explanations of terms, will control. In addition, the materials, methods, and examples are illustrative only and not intended to be limiting.

I. Overview of Several Embodiments

Disclosed herein are bioreactors that include a container, for example, a tube-like structure aligned on a vertical axis, wherein at least a portion of the container is oriented at an angle relative to the vertical axis, wherein the angle is from about 0° to 90°. In some embodiments, the container is placed on a support structure with portions oriented at alternating angles, such that the configuration suggests an accordion (e.g., FIGS. 2 and 3B).

In some embodiments, a disclosed bioreactor includes:

(a) a container for holding fluid comprising a first sheet and a second sheet, wherein the second sheet is disposed adjacent to the first sheet and the first and second sheets are sealed along a first longitudinal edge, a second longitudinal edge, a first horizontal edge, and a second horizontal edge, and comprising at least one opening in the second horizontal edge;

(b) a support structure comprising at least two vertical supports and at least two horizontal supports, wherein portions of the container of part (a) are alternately positioned in front of and behind the at least two horizontal supports, wherein an angle relative to the vertical axis is formed in the container, wherein the angle is about 0° to about 90° and at least one of the angles is different than 0°; and (c) a means for introducing gas and providing mixing connected to the at least one opening in the second horizontal edge.

In some examples the first sheet and the second sheet are a flexible material, such as a flexible plastic, for example plastic sheeting. In particular examples, the sheets are flexible polyethylene, polyvinyl chloride, polypropylene, polyurethane, high density polyethylene, or polyacrylate. In some examples the sheets are about 1 mil to about 20 mil thick (such as about 2 to 10 mil, about 3 to 5 mil, or about 5 to 15 mil). In a specific example, the sheets are polyethylene. In other examples, the first and second sheets are a rigid material such as glass, Plexiglas, polycarbonate, or polyvinyl chloride. In some examples the rigid material is plastic (such as polyvinyl chloride or polycarbonate) having a thickness of about 0.5 mm to about 10 mm (such as about 1 to 10 mm or 2.5 to 7.5 mm). In other examples, the rigid material is glass having a thickness of about 1 mm to about 7.5 cm (for example about 10 mm to 5 cm or about 1 cm to 5 cm). In further examples, the first sheet and the second sheet are different materials. For example, the first sheet is a flexible material (for example, flexible polyethylene or polyvinyl chloride) and the second sheet is a rigid material (for example, rigid polyvinyl chloride or polycarbonate), or vice versa.

In further examples, at least one of the first and second sheets (for example, one or both) are transparent. In a particular example, both the first sheet and the second sheet are transparent. A transparent sheet is one that allows light of selected wavelengths to pass through (such as light of about 200 to 1000 nm or about 400 to 700 nm). In some examples, the transparent first and/or second sheets allow light of about 200 nm to 1000 nm to pass through. In some non-limiting examples, at least one of the first and second sheets (for example, one or both) allow photosynthetically active radiation (for example, wavelengths of light between about 400-700 nm) to pass through the sheet. In other examples, at least one of the first and second sheets (for example, one or both) are translucent or opaque (such as reflective). One of skill in the art can select appropriate materials and levels of transparency for the first and/or second sheets depending on the cells to be cultured in the bioreactor.

The size of the first and second sheets (or the premade tube or flattened rectangle, discussed below) is selected to produce a bioreactor of a desired size. In some examples, the width of the first and second sheets (for example, from the first longitudinal edge to the second longitudinal edge) is about 2.5 cm to about 5 m (for example, about 5-25 cm, about 10-50 cm, about 0.25-2 m, about 0.5-1 m, about 1-2 m, or about 2-5 m). In a particular example, the width of the first and second sheets is about 0.5 m. The material, thickness, and size of the sheets is selected such that the bioreactor does not substantially deform (for example, sag) or burst when the bioreactor is in operation. One of skill in the art can select suitable materials based on the expected weight of the bioreactor in operation, the arrangement of the support structure (discussed below), and the size of the chambers.

In some embodiments, the first sheet and the second sheet are disposed adjacent to one another. In some examples, the longitudinal (long) edges of the first and second sheet are closed or sealed, for example, along a first longitudinal edge and along a second longitudinal edge. The closure or seal is such that fluid that is between the first and second sheet cannot escape through the longitudinal edges. In one example, the longitudinal edges of the first and second sheets are sealed using a heat seal. In another example, the longitudinal edges of the first and second sheets are sealed using an adhesive. In some examples, the first longitudinal edge and/or the second longitudinal edge is sealed completely, while in other examples, at least one opening is included in one or both of the longitudinal edges. For example, one or both of the longitudinal edges may have one or more (such as 2, 3, 4, 5, or more) openings or ports for air venting, adding or removing cell culture medium and/or cells, sensor placement, and so on. In some examples, the opening includes a cap, lid, valve, or other replaceable closure, such that the opening can be closed or substantially closed during operation of the bioreactor.

In some embodiments, the first and second sheets are also sealed along a first horizontal edge (for example, the "top" edge). In some examples, the first horizontal edge is sealed completely, while in other examples, at least one opening is included in the first horizontal edge. For example, the first horizontal edge may have one or more (such as 2, 3, 4, 5, or more) openings or ports for air venting, adding or removing cell culture medium and/or cells, sensor placement, and so on. In some examples, the opening includes a cap, lid, valve, or other replaceable closure, such that the opening can be closed or substantially closed during operation of the bioreactor. As discussed below, the second horizontal edge is not sealed completely, and includes at least one opening. When sealed along the first longitudinal edge, the second longitudinal edge, the first horizontal edge, and the second horizontal edge, the first and second sheets form a rectangle or a flattened tube. In some examples, the first and second sheets are at least 0.25 meters in length (such as at least about 0.5, about 0.75, about 1, about 1.25, about 1.5, about 1.75, about 2, about 2.25, about 2.5, about 2.75, about 3, about 4, about 5, or more meters in length). In some examples, the first and second sheets are about 1-10 meters in length, such as about 1-5 meters, about 1-3 meters, or about 1.5-2.5 meters in length.

In other embodiments, the first and second sheets are formed from a continuous sheet of flexible material. In some examples, the first sheet and second sheet are produced or obtained as a tube or a cylinder (or a rectangle, when flattened). In this case, what would be the first and second longitudinal edges in the case of separate first and second sheets, are already sealed (e.g., are continuous) and the tube is open at the ends (for example, unsealed at the top and the bottom edges). A tube or flattened rectangle of the desired length (or height) can be obtained (for example, cut from a larger piece) and then sealed at the top and bottom edges (e.g., first and second horizontal edges) as described herein (for example, leaving at least one opening in the bottom edge, and optionally one or more openings in the top edge). In some examples, the tube or flattened rectangle is polyethylene.

In other examples, a continuous sheet of the material is folded along a midpoint, such that the fold forms the first (or second) horizontal edge. The material on one side of the fold forms the first sheet and the material on the other side of the fold forms the second sheet, which is disposed adjacent to the first sheet. The longitudinal edges are sealed and the open horizontal edge is sealed, forming a bottom seal with at least one opening, as discussed below. In other examples, a continuous sheet of the material is folded along a midpoint, such that the fold forms the first (or second) longitudinal edge. The material on one side of the fold forms the first sheet and the material on the other side of the fold forms the second sheet, which is disposed adjacent to the first sheet. The second (or first) longitudinal edge is sealed and the open horizontal edges are sealed as discussed herein.

The bottom of the first and second sheets (the second horizontal edge) is sealed in such a way as to leave at least one opening (such as 1, 2, 3, 4, or more openings) in the bottom edge. In some examples, the bioreactor includes at least one bottom seal that is angled, for example upwardly or downwardly from horizontal (for example, with respect to the first horizontal edge). In some examples, the angle is from about 30° to about 160° from horizontal. In one particular example, the bottom edge has two angled seals which slope toward each other (for example, in a conical or "V" shape), but do not meet, leaving an opening in the bottom edge. In other examples, the bottom edge is formed from one or more horizontal seals, with at least one opening (such as 1, 2, 3, 4, or more openings). In some embodiments, the opening is approximately centered along the bottom edge, while in other embodiments, the opening is closer to the first longitudinal edge than to the second horizontal edge, or vice versa. In examples with two or more openings on the bottom edge, the openings may be evenly spaced along the bottom edge or may be grouped together or spread apart. One of skill in the art can select appropriate positioning and spacing of the openings, depending on the dimensions of the bioreactor and the particular use for the bioreactor.

In some examples, the at least one opening in the bottom edge is at least 0.5 cm wide (for example, at least about 1 cm, about 1.5 cm, about 2 cm, about 2.5 cm, about 5 cm, about 7.5 cm, about 10 cm, or more). In a particular example, the opening is about 2.5 cm wide or about 5 cm wide. In other examples, the size of the one or more openings in the bottom edge is about 1-25% of the width of the bottom edge (such as about 5-25%, about 1-15%, about 5-15%, about 1-10%, about 1-5%, or about 2-5%).

In some embodiments, the disclosed bioreactors also include at least one means or delivery device for providing carbon dioxide, air, other gases, and/or nutrients to the culture in the bioreactor. In some examples, the at least one delivery device is attached to or placed in an opening along the bottom edge of the tube-like or rectangular structure formed from the first and second sheets sealed as described above. In some examples, the delivery device includes a gas sparger or diffuser. One of skill in the art can select appropriate gases and/or nutrients and their concentrations based on the organism, cell, or tissue present in a bioreactor of the disclosure. The sparger or diffuser may be attached directly to the opening, or indirectly attached, for example by a tube or other connector.

In some examples, for example when air and/or fluid are present in the resulting flattened tube or rectangle produced by sealing the first and second sheets as described above, the distance between the first sheet and the second sheet is about 5 mm to about 50 cm. In particular examples, the distance between the first sheet and the second sheet is about 1 cm to about 30 cm (such as about 1 to 20 cm, about 1 to 15 cm, about 2 to 10 cm, about 2 to 8 cm, about 1 to 5 cm, or about 2 to 6 cm) when the bioreactor is in operation. In one specific example, the distance between the first and second sheet when the bioreactor is in operation is about 6 cm. In some examples, the distance between the first and second sheets is not constant over the entire length of the bioreactor. For example, the distance between the first and second sheets may be decreased at points where the sheets are contacted by the horizontal supports (see, e.g., FIG. 3B).

In some embodiments, the disclosed bioreactors optionally include at least one intermediate horizontal seal (such as 2, 3, 4, 5, 6, 7, 8, 9, 10, or more) located between the first horizontal edge and the second (bottom) edge, forming at least two chambers for holding fluid in series along a vertical axis. In some examples, the intermediate horizontal seal is substantially horizontal, for example substantially parallel with the first and second horizontal edges. In other examples, the intermediate horizontal seal is angled, for example upwardly or downwardly from horizontal (for example, with respect to the first (top) horizontal edge). In some examples, the angle is from about 30° to about 160° from horizontal. In other examples, the bioreactor includes a combination of orientations of the intermediate horizontal seals (such as horizontal, upwardly angled, downwardly angled, or any combination of two or more thereof). Each intermediate horizontal seal includes at least one opening that allows communication of air and/or fluid between the two chambers formed by the intermediate horizontal seal. In some examples, the intermediate horizontal seal is formed (at least in part) by pressure from an exterior structure, such as the horizontal supports (discussed below). In other examples, the intermediate horizontal seal is formed using a heat seal or an adhesive.

In some embodiments, the surface area and volume of the bioreactor are chosen to maintain a positive surface area to volume ratio. The surface area is the total surface area of the first and second sheets (the sum of the total length times total width for each sheet). The total volume is the total liquid volume that is held in the compartment formed by the sealed first and second sheets. In particular examples, the bioreactor has a total surface area:volume ratio of about 5:1 to about 500:1.

A bioreactor disclosed herein also includes a support structure that holds the first and second sheets. In some embodiments, the support structure includes at least two vertical supports and least one horizontal support that extends between the two vertical supports. In some examples, the bioreactor includes four vertical supports (for example in a square or rectangular arrangement) with horizontal supports connected between two vertical supports (for example, one or more horizontal supports extend between two of the vertical supports and one or more horizontal supports extend between the other two vertical supports). In some examples, the support structure may include one or more intermediate vertical supports, depending on the length of the horizontal supports. One of skill in the art can select the number and arrangement of vertical and horizontal supports based on the size and arrangement of the bioreactor.

In some examples, the top of the tube-like structure formed from the first and second sheets as described above (for example the first horizontal edge) is attached to the support structure at a height such that the one or more openings at the bottom edge do not touch the ground or floor. The tube-like structure is disposed over or under (in front of or behind) the horizontal support(s) such that each portion of the tube that is between the horizontal supports is approximately vertical (0° relative to the vertical axis) or at an angle relative to the vertical axis (for example from greater than about 0° to 90°). The horizontal supports are in contact with either the first or second sheet. Exemplary arrangements are shown in FIGS. 2, 3A-3B, and 4. In some examples, the horizontal support may compress the first or second sheet, for example decreasing the distance between the first and second sheet. In some examples, the horizontal support decreases the distance between the first and second sheet by no more than 95% (for example, no more than 90%, 85%, 80%, 75%, 70%, 65%, 60%, 55%, 50%, 45%, 40%, 35%, 30%, 25%, 20%, 15%, 10%, 5%, or less). In embodiments with one or more intermediate horizontal seals, the support structure includes at least one horizontal support located at or near the level of the horizontal intermediate seal. In one example, a horizontal support is placed just above the level of a horizontal intermediate seal. In another example, a horizontal support is placed at about the same level as an intermediate horizontal seal. In further examples, a horizontal support is placed just below the level of an intermediate horizontal seal.

The horizontal and vertical supports are adjustable, so that the formation of the angles can be altered simply and easily. In some examples, the angle is about 20° to about 80°, about 30° to about 75°, or about 45° to about 65°. In other examples, the angle is about 5°, 10°, 15°, 20°, 25°, 30°, 35°, 40°, 45°, 50°, 55°, 60°, 65°, 70°, 75°, 80°, 85°, or 90°. Each angle formed in the bioreactor by its disposition over or under a horizontal support may be independently selected and is adjustable, such that the angles can be optimized for particular growing conditions (such as light conditions or cell type being cultured). In some examples, at least one portion of the tube (e.g., at least one compartment) is oriented at an angle of about 0° relative to the vertical axis. In one particular example, a bioreactor has a configuration such that the angles alternate between about 0° relative to the vertical axis and an angle greater than 0° relative to the vertical axis. In other examples, none of the angles are about 0° relative to the vertical axis (for example, all of the angles are greater than 0° relative to the vertical axis). As described herein, an "angle of about 0° relative to the vertical axis" does not require an absolutely vertical orientation. Thus, for example, an angle of about 0° relative to the vertical axis is substantially vertical. In some examples, the angle may be up to about 2° relative to vertical (for example, about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, or 2° relative to the vertical axis, e.g., FIG. 4) and be considered to be substantially vertical. As described herein, an "angle of about 0°" is considered to be about 0° relative to the vertical axis, or substantially vertical.

One of skill in the art can select a suitable support structure. In some examples, commercial rack units are utilized. In other examples, a support structure can be constructed from readily available materials, such as polyvinyl chloride pipe or rods, metal bars or rods, or wooden bars or rods. In some examples, the support structure is about 1-4 meters in height. In other examples, the support structure is at least about 1, 1.5, 2, 2.5, 3, 3.5, 4, 4.5, 5, or more meters in height. In some examples, the at least one horizontal support is about 10 cm to about 10 m long (such as about 20 cm to 5 m, 50 cm to 2.5 m, or about 1 m). In other examples, the horizontal support may be more than 10 m long (for example about 10, 25, 30, 25, 30, 40, 50, 60, 70, 80 90, 100 m, or more), provided that the material has sufficient strength to support the tube (including liquid and cells) without substantial bending or sagging. As discussed above, if longer horizontal supports are utilized, intermediate vertical supports can also be used to provide sufficient strength to support the operating bioreactor(s) containing liquid and cells. One of skill in the art can select an appropriate material (for example metal, plastic, or wood) according to the desired length and weight to be supported.

In some embodiments one or more sensors are optionally included in the bioreactors. In some examples, sensors and instrumentation are included to monitor one or more parameters of the cell culture, the environment, or both. Culture parameters that may be monitored include water (or other liquid) temperature, electrical conductivity, pH, carbon dioxide, dissolved oxygen, optical density (e.g., cell density), ion concentration (e.g., calcium concentration), and flow rate. Environmental parameters that may be monitored include air temperature, relative humidity, solar radiation, photosynthetic active radiation, and wind speed. One of skill in the art can identify additional parameters that may be desirable to monitor, depending on the size, type, or location of the bioreactor or the type of cell culture being carried out. The sensors for measuring culture parameters are placed in one or more locations in the system. One of skill in the art can select appropriate numbers and locations for sensors for any particular parameter. One or more sensors for monitoring environmental parameters are placed in close proximity to the bioreactor, such as within at least 50 meters of the bioreactor.

In additional embodiments, the disclosed bioreactors include means for regulating temperature of a culture in the bioreactor. In some examples, a bioreactor includes a heating or cooling jacket (for example integrated in one of the first and second sheets) that can be used to regulate the temperature of a culture. Means of regulating temperature of a bioreactor are well known to one of skill in the art and include heat exchangers, such as by circulating a heated or chilled liquid through a jacket in order to maintain a constant selected temperature. In some examples, a third sheet of transparent material (such as flexible plastic sheeting) is placed over one or both of the first and second sheets, creating a second layer that fluid (such as water of a desired temperature) is circulated through. The thickness of the layer and the fluid are selected such that there is not a substantial decrease in light passing through the second layer to the space between the first and second sheet. In other examples, temperature regulation is achieved by spraying the outer surface of the bioreactor with a fluid (such as water), or by using a fan and pad cooling system, creating evaporative cooling. In some examples, heat for a heating jacket or heat exchanger is waste heat, for example from a biogasification system, solar cell waste heat unit, power plant, geo-thermal source, or industrial plant located near the system. In other examples, heat is provided from warm water. In further examples, the temperature regulation device includes at least one cooling pipe, such as a pipe for circulating cool water.

Figure 4:
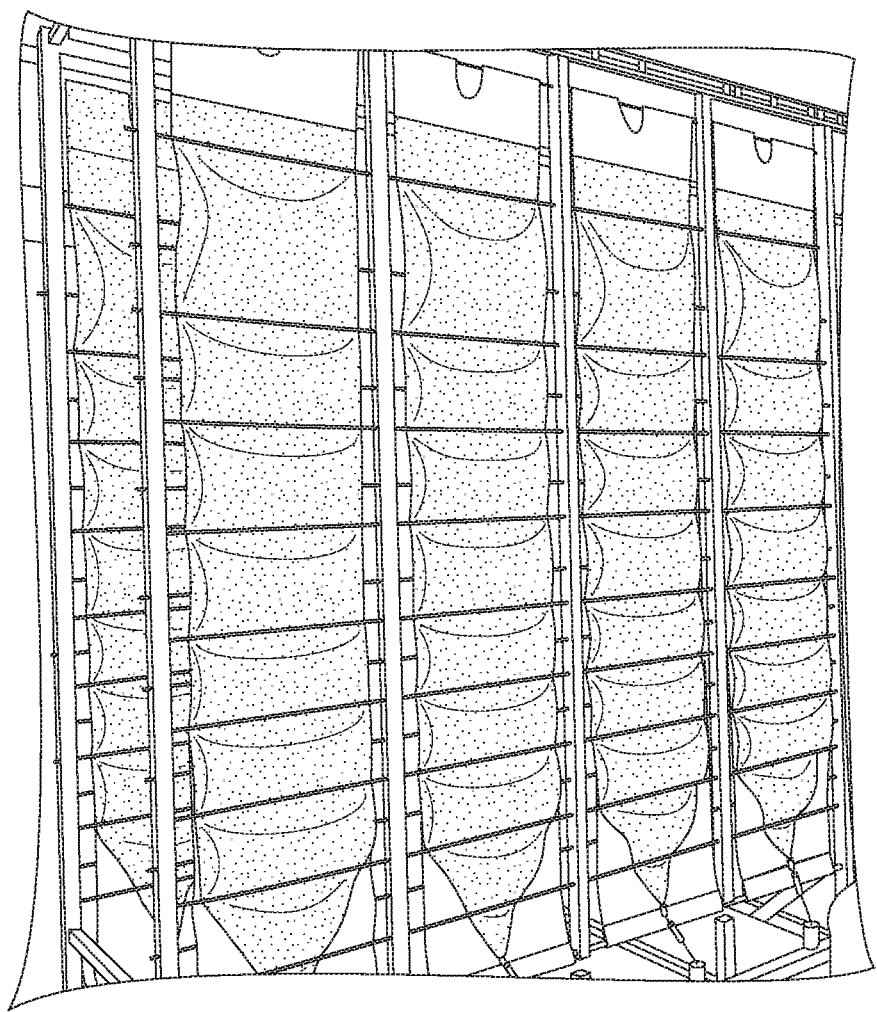
FIG. 4 is a digital image of an exemplary large scale embodiment of Air Accordion bioreactors in operation.

The disclosed bioreactors can be arranged in a modular fashion. For example, a common structural support (such as the at least one horizontal support) can be used to support multiple vertical series of chambers as described above. FIG. 4 shows an exemplary modular system with two rows of four bioreactors. The number of bioreactors can be selected by one of skill in the art based on the desired level of production of culture, size of the bioreactors, and size of the support structure. In some non-limiting examples, the number of bioreactors is 2 or more (such as 3, 4, 5, 6, 7, 8, 9, 10, 20, 50, 100, or more), for example 2-100 (such as 5-30, 10-20, 25-50, 40-80, or 50-100). In particular examples, the modular system includes at least two vertical supports and at least one horizontal support that extends between the vertical supports. In other particular examples, the modular system includes at least four vertical supports (for example, in a rectangular configuration) and at least one horizontal support that extends between two of the vertical supports.

In some examples, a system including two or more bioreactors shares one or more delivery devices for providing carbon dioxide, air, other gases, and/or nutrients to the culture. In other examples, each of the bioreactors has a separate delivery device for providing carbon dioxide, air, other gases, and/or nutrients to the culture.

II. Description of Particular Embodiments

In the embodiments provided herein and described below, it is to be understood that the drawings are exemplary only and are not necessarily shown to scale. Any of the features described herein (for example, length and/or width of the sheets, size of openings, size of chambers, angles, size of structural supports, and so on) can be adjusted by one of skill in the art utilizing the present disclosure.

FIG. 1 is a flattened elevation view of an exemplary embodiment of a bioreactor system 100 of the disclosure. The bioreactor includes a first sheet 110 disposed adjacent to a second sheet (not shown) which are closed or sealed along a first longitudinal edge 120 and a second longitudinal edge 125. The first sheet 110 and the second sheet (not shown) are also closed or sealed along a first horizontal edge 130. The first sheet 110 and second sheet (not shown) are also sealed along a first angled edge 140 and a second angled edge 145. The first angled edge 140 and the second angled edge 145 do not meet, forming an opening 150 at the bottom. In some embodiments, a gas sparger or diffuser (not shown) is connected directly or indirectly to the opening 150. The bioreactor system 100 also includes a support structure that includes at least two horizontal supports 160 that are positioned between at least two vertical supports 170. The first and second sheets, sealed as described above, are positioned such that the horizontal supports alternate being behind 160a and in front of 160b the sheets and result in an angle of the first and second sheets from the vertical axis 180 (as shown in FIG. 2).

Figure 2:
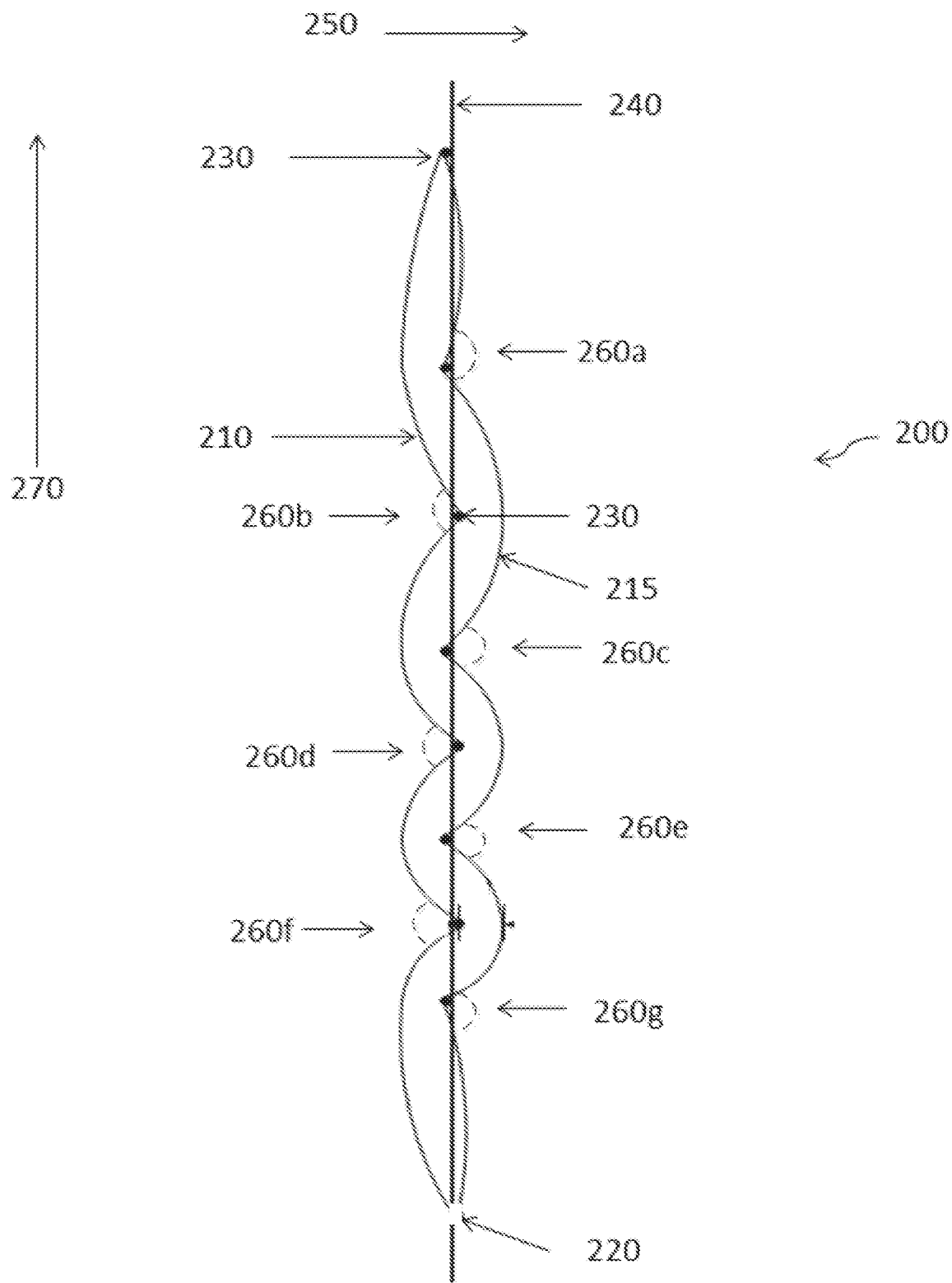
FIG. 2 is a side view of an exemplary bioreactor of the disclosure.

FIG. 2 is a side view of an exemplary embodiment of a bioreactor system 200 of the disclosure. A first sheet 210 is disposed adjacent to a second sheet 215 and sealed except for an opening 220 at the bottom. In some embodiments, a gas sparger or diffuser (not shown) is connected to the opening 220. As shown in this view, at least some of the horizontal supports 230 (which are attached to a vertical support 240) are offset in a horizontal axis 250 to dispose the first sheet 210 and second sheet 215 at an angle 260 relative to the vertical axis 270. Each of the angles (260a, 260b, 260c, 260d, 260e, 260f, and 260g) can be different, or two or more can be the same.

III. Methods of Culturing Cells in an Air Accordion Bioreactor

Disclosed herein are methods of culturing cells in a bioreactor utilizing embodiments of the bioreactors and systems described above.

In one embodiment, the methods include incubating a suspension of cells in a nutrient solution in a bioreactor of the present disclosure. In another embodiment, the methods include incubating cells or tissue in culture medium in a bioreactor of the disclosure. The methods include batch culture, semi-continuous culture, or continuous culture of the cell, tissue, and/or organism of interest. Liquid medium and/or cells are introduced into the bioreactor through one or more openings in the first and/or second sheets, such as one or more openings in the first horizontal (top) edge, second horizontal (bottom) edge, first longitudinal edge, or second longitudinal edge. During operation of the bioreactor, samples can be collected through the one or more openings in any of the edges, including the first horizontal (top) edge, first or second longitudinal (side) edges, or the second horizontal (bottom) edge.

In some examples, mixing and aeration of the cell suspension or culture medium containing cells or tissue is provided by a delivery device for providing carbon dioxide, air, other gases, and/or nutrients, such as one or more gas spargers or diffusers, connected to the one or more openings at the bottom edge of the bioreactor. Gas bubbling from the sparger or diffuser through the culture medium provides mixing and gas transfer. The gas flow rate is adjusted to provide adequate mixing and aeration for cell growth. In some examples, the gas flow rate provides mixing such that the cells in the culture medium do not appreciably settle, but remain in suspension. The gas flow rate is adjusted to provide sufficient mixing, without causing substantial damage to the cells, for example from shear stress. In particular examples, the methods include sparging the cell suspension or the culture medium (for example, in the case of tissue or organ culture) with a mixture of 5% $CO_2$/95% air. Appropriate gas mixtures can be selected by one of the skill in the art based on the type of cell or tissue/organ that is being cultured. One of skill in the art can also select appropriate gas flow rates for the particular application (such as the particular cells being cultured). Exemplary gas flow rates include about 0.01 liters/liter/min ($LL^{-1}min^{-1}$) to about 2 $LL^{-1}min^{-1}$ (such as about 0.01 $LL^{-1}min^{-1}$ to about 0.1 $LL^{-1}min^{-1}$, about 0.01 $LL^{-1}min^{-1}$ to about 0.05 $LL^{-1}min^{-1}$, about 0.01 $LL^{-1}min^{-1}$ to about 1.5 $LL^{-1}min^{-1}$, about 0.01

$LL^{-1}min^{-1}$ to about 1 $LL^{-1}min^{-1}$, about 0.01 $LL^{-1}min^{-1}$ to about 0.05 $LL^{-1}min^{-1}$, about 0.05 $LL^{-1}min^{-1}$ to about 0.5 $LL^{-1}min^{-1}$, about 0.1 $LL^{-1}min^{-1}$ to about 1 $LL^{-1}min^{-1}$, about 0.5 $LL^{-1}min^{-1}$ to about 2 $LL^{-1}min^{-1}$, about 1 $LL^{-1}min^{-1}$ to about 2 $LL^{-1}min^{-1}$). In particular examples, the gas flow rate is about 0.01 $LL^{-1}min^{-1}$ to about 0.05 $LL^{-1}min^{-1}$, for example, about 0.01 $LL^{-1}min^{-1}$, about 0.015 $LL^{-1}min^{-1}$, about 0.02 $LL^{-1}min^{-1}$, about 0.025 $LL^{-1}min^{-1}$, about 0.03 $LL^{-1}min^{-1}$, about 0.035 $LL^{-1}min^{-1}$, about 0.04 $LL^{-1}min^{-1}$, about 0.045 $LL^{-1}min^{-1}$, or about 0.05 $LL^{-1}min^{-1}$.

In some embodiments, the method includes exposing the bioreactor, and the culture in the bioreactor to a light source, for example for culture of photosynthetic cells, such as algae or microalgae cells. In some examples, the light source is natural sunlight. For example, the bioreactor may be placed outdoors or in a greenhouse where it is exposed to natural sunlight. In this example, the culture is exposed to natural light/dark cycles, which vary in length according to latitude and season. In other examples, the bioreactor and culture is exposed to an artificial light source (for example, incandescent, fluorescent, or halogen lamps, or light emitting diodes). If the light source is an artificial light source, the method may include alternating periods of light and dark. In one non-limiting example, the bioreactor is exposed to light for 12 hours of a 24 hour cycle.

In some examples, the wavelength of the light source (such as an artificial light source) is selected to promote optimal growth of the organism or cell type in culture in the bioreactor. In some examples, the wavelength of the light source includes or consists of photosynthetically active radiation (for example, wavelengths of light between about 400-700 nm). In other examples, the wavelength of the light source is selected to induce or increase synthesis of one or more compounds of particular interest by the organism or cell in culture. For example, synthesis of anthocyanin is induced by UV-B light (such as about 280-300 nm). One of skill in the art can select appropriate lights or wavelengths for culture of cells and/or production of compounds of interest, for example to maximize cell growth or production.

In some examples, the angle of each portion of the bioreactor (referred to in some examples herein as a chamber or compartment) disposed on the horizontal supports relative to the vertical axis is selected to optimize the exposure of the portion of the bioreactor (and the culture within) to incident light. In some examples, the angle is selected such that the irradiance is about 80 to 500 $\mu mol/m^2 s$. One of skill of the art can select an appropriate irradiance range, based on the cell or organism that is in culture in the bioreactor. In some examples, an irradiance of about 80-250 $\mu mol/m^2 s$ is selected if microalgae cells are in culture. In other examples, an irradiance of about 300-400 $\mu mol/m^2 s$ is selected if plant cells or plant tissue is in culture. In some examples (for example, if the bioreactor is exposed to natural sunlight), the angle necessary to achieve a selected irradiance may change over time. The bioreactor can be adjusted (for example, by moving one or more horizontal supports) in order to change one or more of the angles to achieve or maintain a selected irradiance level. In some examples, this is achieved by manually adjusting the bioreactor. In other examples, an automated system is used to periodically or continuously adjust the angle(s) to achieve or maintain the selected irradiance.

In some examples, the method includes regulating the temperature of the culture. Means for temperature regulation are well known to one of skill in the art. In one example, the bioreactor is in an enclosed area (such as a greenhouse) which is heated or cooled to maintain a selected temperature or range of temperatures. In other examples, the temperature of the culture may be regulated by a temperature regulation device in the culture medium or around the bioreactor. Such devices include heating or cooling jackets or heat exchangers (as discussed in section I, above). In particular examples, heat is provided at night in order to maintain the temperature of the culture in an optimal range for growing the culture. In other examples, cooling is provided during the day (particularly at times of day or seasons with high solar radiation) in order to maintain the temperature of the culture in an optimal range. One of skill in the art can select appropriate temperature ranges for the particular cell or organism in culture and determine the need for heating or cooling to maintain the selected temperature range.

In some embodiments, the method also includes harvesting the culture. The culture may be harvested when a selected parameter is reached, for example a time point (for example, at least about 6, 12, 24, 36, or more hours of culture, such as at least 1, 2, 3, 4, 5, 6, 7, or more days of culture), cell density (for example, at least about $10^3$, $10^4$, $10^5$, $10^6$, or more cells per milliliter), or optical density of the culture (for example, absorbance of at least about 0.5, 1.0, 1.5, 2, 2.5, or more at a selected wavelength, such as 750 nm). One of skill in the art can select appropriate parameters or time points for culture harvest, based on the organism or cell type being cultured.

Methods for harvesting cells are well known to one of skill in the art. In some examples, the entire culture is harvested. In other examples, a portion of the culture is retained for use as inoculum for continued culture production. For example, culture is stored for use as an inoculum and water or culture medium is subsequently added to the bioreactor to start the new culture batch. In some examples, the culture stored for inoculum use is about 100 ml to about 100 liters (such as about 1-50 liters, 10-75 liters, 25-75 liters, or about 30-40 liters). In other examples, a proportion of the culture is retained for inoculation of the new culture, for example about 10-80% of the total harvested culture volume (such as about 10-40%, 10-35%, 20-50%, 20-40%, 30-70%, 40-60%, 30-35%, or about 33% of the total harvested culture volume). The volume or percentage of the culture needed for use as inoculum can be determined by one of skill in the art, for example, based on the cell or organism in culture, the density of the culture at harvesting, and the total volume of liquid that will be inoculated.

The bioreactors and methods disclosed herein are suitable for culturing a wide variety of organisms or cells, including, but not limited to algae (such as microalgae and/or macroalgae). In some examples, the algae species include, but are not limited to *Chlorella* (such as *Chlorella vulgaris*), *Chlamydomonas* (such as *Chlamydomonas reinhardtii*), *Chaetoceros, Spirulina* (such as *Spirulina platensis*), *Dunaliella*, and *Porphyridum*. In particular examples, the algae species include algae useful for production of biofuels or other compounds (such as polyunsaturated acids, pigments, or phytochemicals, for example, for nutritional supplements). In some examples, the algae include *Akistrodesmus, Arthrospira, Botryococcus braunii, Chlorella* (such as *Chlorella* sp. or *Chlorella protothecoides*), *Crypthecodinium* (such as *Crypthecodinium cohnii*), *Cyclotella, Dunaliella tertiolecta, Gracilaria, Hantzschia, Haematococcus* (such as *Haematococcus pluvialis*), *Monodus* (such as *Monodus subterraneous*), *Nannochloris, Nannochloropsis, Neochloris oleoabundans, Nitzschia, Phaeodactylum, Pleurochrysis carterae* (also called CCMP647), *Porphyridium, Sargassum, Scenedesmus* (such as *Scenedesmus*

*obliquus*), *Schiochytrium*, *Stichococcus*, *Tetraselmis suecica*, *Thalassiosira pseudonana*, *Thraustochytrium roseum*, and *Ulkenia* sp. In particular examples, the algae species is *Monodus subterraneous* or *Chlamydomonas reinhardtii*.

The bioreactors and methods disclosed herein are also suitable for culturing any cells that can be grown in suspension, including but not limited to, microalgae (as discussed above), macroalgae, bacteria (e.g., *Escherichia coli*, *Bacillus subtilis*, or *Corynebacterium*), fungi (e.g., *Saccharomyces cerevisiae*, *Kluyveromyces lactis*, or *Pischia pastoris*), insect cells (e.g., *Spodoptera frugiperda* cells (such as Sf9 or Sf21 cells) or *Trichoplusia ni* cells (such as High Five™ cells)), plant cells (such as *Arabidopsis thaliana* cells, *Nicotiana tabacum* cells, or *Taxus* cells), or mammalian cells (such as Chinese hamster ovary (CHO) cells or human embryonic kidney cells (e.g., HEK 293 cells)). In one example, the bioreactors and methods disclosed herein are useful for culturing algae for the production of fatty acids for synthesis of biofuels. In other examples, the bioreactors and methods disclosed herein are useful for culturing cells for the production of other natural products (such as taxols, pigments, or dietary supplements) or recombinant proteins.

The bioreactors and methods disclosed herein may also be used for culture of tissue or organs (such as animal or plant tissue or organ culture). In one example, the bioreactors and methods disclosed herein are used for hairy root culture (for example *Panax ginseng*, *Lithospermum erythorhizon*, *Hyoscyamus muticus*, or *Atropa belladonna*). In other examples, the bioreactors and methods disclosed herein may be used to culture plant tissue, plant organs, or plant somatic embryos. In other examples, the bioreactors and methods disclosed herein may be used to culture mammalian organs or mammalian tissue. In some examples, the tissue or organ is stationary in a portion of a bioreactor and nutrient solution flows through the compartment, submerging or bathing the tissue or organ.

The present disclosure is illustrated by the following non-limiting Examples.

Example 1

Air Accordion Bioreactor Construction

This example describes the construction of an Air Accordion bioreactor.

The Air Accordion bioreactor was a combination of polyethylene tubing sealed at both ends to form the reactor vessel and a supporting frame made of metal. Polyethylene tubing with a width of 0.457 m and a wall thickness of 0.152 mm was used to create the culture vessel. The length of the vessel was 1.78 m for the Air Accordion with an operational volume of 35.0 L. Laboratory flask experiments were conducted in 1-liter Pyrex Roux culture flat bottles (55×120× 255 mm) with an operational volume of 800 ml.

The support frame (2.18 m×0.457 m×1.83 m) was constructed of heavy metal wire combined with cold-rolled iron bars as cross beams. These bars were 1.58 cm in diameter, which was necessary to support the liquid in the bioreactor. Bar spacing was experimented briefly, and was optimized to provide the most even distribution of culture media throughout the bioreactor.

Example 2

Algal Cell Culture in Air Accordion Bioreactor

This example describes culture of algal cells in an Air Accordion bioreactor and comparison of the Air Accordion bioreactor with the Accordion bioreactor (described in U.S. Pat. No. 8,709,808, incorporated herein by reference in its entirety).

*Monodus subterraneous* or *Chlamydomonas reinhardtii* were cultured in an Air Accordion bioreactor (described in Example 1) or an Accordion bioreactor (length of the vessel was 2.08 m with an operational volume of 40.0 L). The bioreactors contained appropriate culture medium and were inoculated with *M. subterraneous* or *C. reinhardtii* that had been cultured in the laboratory. Inoculation concentration was typically 0.01 to 1.0 g/L. *C. reinhardtii* was cultured in High Salt Medium (HSM), while *M. subterraneous* was cultured in Miller-Fogg Optimized Medium (MF). The Air Accordion bioreactor was aerated by a gas sparger connected to the opening at the bottom of the bioreactor with 5% $CO_2$/air at a gas flow rate of 0.0143-0.0286 $LL^{-1}min^{-1}$, as indicated. The Accordion bioreactor had alternating vertical and angled chambers and the culture medium including the cells was recirculated from the bottom to the top of the reactor using a pump with a flow rate of 6.5 LPM or 31.5 LPM, as indicated.

Both reactors were exposed to the same or similar environmental conditions. Reactors in the laboratory were under 24-hour illumination with 8×CWF placed centrally behind the reactor providing light from 21.5 $\mu mol\ m^{-2}\ s^{-1}$ at top and bottom extremes to 250 $\mu mol\ m^{-2}\ s^{-1}$ at the center of the reactor. The laboratory Air Accordion bioreactors were similarly under 24-hour illumination with 8×CWF placed centrally behind the reactor providing, 80 $\mu mol\ m^{-2}\ s^{-1}$ at the extreme top and bottom, to 300 $\mu mol\ m^{-2}\ s^{-1}$ at the center of the reactor. Greenhouse experiments were conducted using daytime (7 am to 7 pm) solar radiation that ranged from 50 to 1200 $\mu mol\ m^{-2}\ s^{-1}$ (400-700 nm) with a daily average of 500-600 $\mu mol\ m^{-2}\ s^{-1}$ (400 nm-700 nm). This was supplemented with night time illumination equivalent to the laboratory of 8×CWF placed centrally. In the laboratory the room temperature remained in the range of 26±1.5° C. The greenhouse temperature was maintained by means of evaporative cooling pads and remained around 28±3° C. Samples were collected periodically and cell concentration, biomass, and chlorophyll content were measured.

Figure 5:
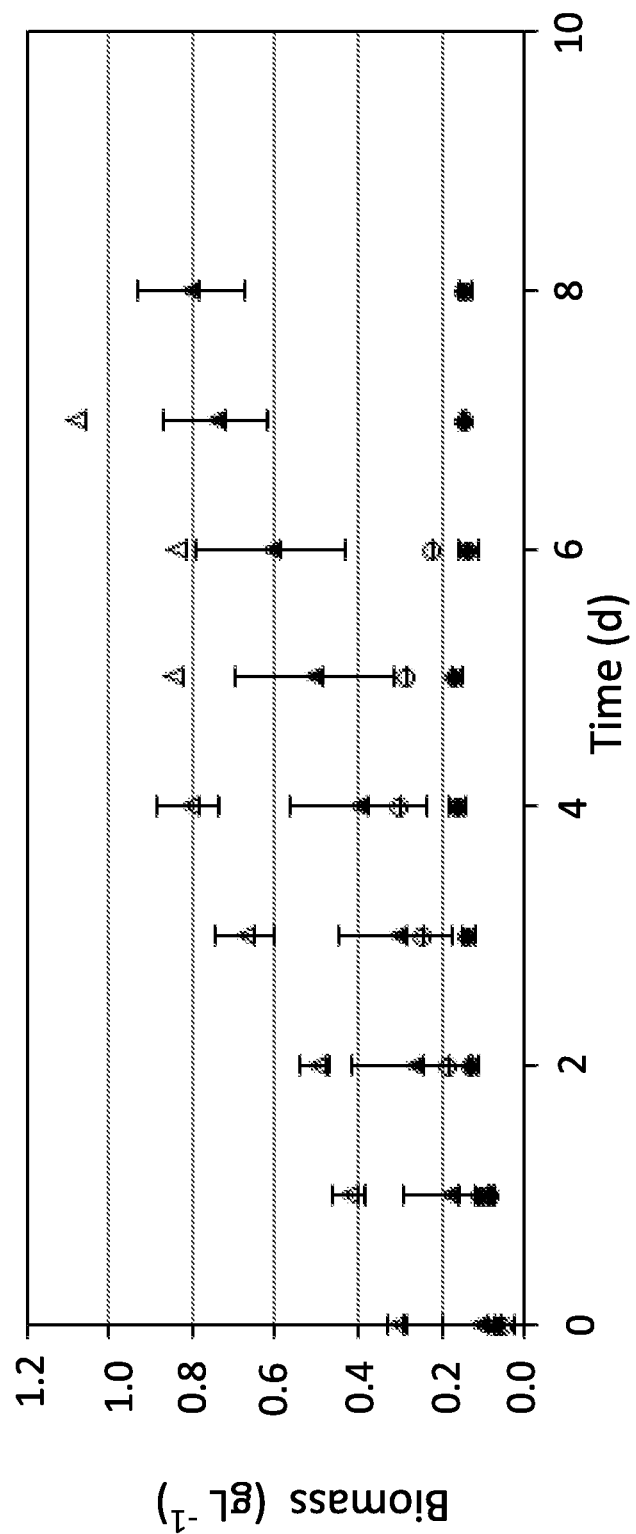
FIG. 5 is a graph showing growth of *Monodus subterraneus* in an Accordion bioreactor with a diaphragm pump at 6.5 liters per minute (LPM) flow (open circles), an Accordion bioreactor with an impeller pump at 31.5 LPM flow (closed circles), an Air Accordion bioreactor with gas flow rate of 0.0143 $LL^{-1}min^{-1}$ (closed triangles), and an Air Accordion bioreactor with gas flow rate of 0.0286 $LL^{-1}min^{-1}$ (open triangles).

*M. subterraneous* was cultured in an Air Accordion bioreactor with gas flow rate of either 0.0143 $LL^{-1}min^{-1}$ or 0.0286 $LL^{-1}min^{-1}$ or in an Accordion bioreactor with a flow rate of either 6.5 LPM or 31.5 LPM. Samples were collected daily and biomass was determined. As shown in FIG. 5, the biomass continued to increase in the Air Accordion bioreactor to day 7 or 8, while the biomass accumulation plateaued in the Accordion bioreactor around day 4.

Growth characteristics of *C. reinhardtii* and *M. subterraneous* in Air Accordion and Accordion bioreactors are shown in Table 1. As indicated, in one example, the Air Accordion bioreactor was in a greenhouse during culture, rather than in a laboratory.

TABLE 1

Growth of *Chlamydomonas reinhardtii* and *Monodus subterraneous* in Air Accordion or Accordion bioreactors.

| | Starting cell conc. (g/L) | Max. cell conc. (g/L) | Max. biomass product. (g/L/day) | Max. chlorophyll (mg/L) | Avg. specific growth rate (day$^{-1}$) | Avg. productivity (g/L/day) |
|---|---|---|---|---|---|---|
| *Chlamydomonas reinhardtii* | | | | | | |
| Accordion (31.5 LPM) | 0.008 ± 0.000 | 0.362 ± 0.01 | 0.07 ± 0.02 | 16.7 ± 1.53 | 0.35 ± 0.014 | 0.050 ± 0.001 |
| Accordion (18.9 LPM) | 0.06 ± 0.015 | 0.2 ± 0.032 | 0.075 ± 0.017 | 8.7 ± 0.07 | 0.5728 ± 0.034 | 0.058 ± 0.015 |
| Air Accordion (0.0143 LL$^{-1}$min$^{-1}$) | 0.08 | 0.5 | 0.166 | 27.26 | 0.496 | 0.087 |
| *Monodus subterraneus* | | | | | | |
| Accordion (31.5 LPM) | 0.065 ± 0.007 | 0.163 ± 0.014 | 0.036 ± 0.023 | 2.94 ± 0.4 | 0.0745 ± 0.03 | 0.025 ± 0.005 |
| Accordion (6.8 LPM) | 0.05 | 0.3 | 0.1 | 3.4 | 0.139 | 0.063 |
| Air Accordion (0.0143 LL$^{-1}$min$^{-1}$) | 0.11 ± 0.085 | 0.8 ± 0.13 | 0.128 ± 0.054 | 35.54 ± 18.2 | 0.302 ± .133 | 0.088 ± 0.004 |
| Air Accordion (0.0286 LL$^{-1}$min$^{-1}$) | 0.31 ± 0.023 | 1.08 ± 0.06 | 0.24 ± 0.004 | 36.6 ± 6.6 | 0.179 ± 0.003 | 0.110 ± 0.005 |
| Air Accordion (0.0143 LL$^{-1}$min$^{-1}$) [Greenhouse] | 0.045 ± 0.002 | 2.58 ± 0.002 | 0.212 ± 0.04 | 78.104 ± 4.4 | 0.142 ± 0.007 | 0.098 ± 0.000 |

Example 3

Resource Usage by Air Accordion Bioreactor

This example describes resources consumed by the Air Accordion bioreactor and comparison with resource usage by other bioreactors.

The energy demand of the Air Accordion for aeration and mixing (using gas sparging) was calculated and compared with the energy demand for aeration and mixing of the Accordion bioreactor (using a recirculation pump). As shown in Table 2, the Air Accordion bioreactor used dramatically less total energy per volume than the Accordion bioreactor.

TABLE 2

Energy demand for aeration and mixing in Accordion bioreactor and Air Accordion bioreactor.

| Reactor | Gas flow rate (LL$^{-1}$min$^{-1}$) | Gas flow energy per volume (W/L) | Pump energy per volume (W/L) | Total energy per volume (W/L) |
|---|---|---|---|---|
| Accordion (31.5 LPM) | 5% CO$_2$/Air 0.0125–0.025 | 6.13E−06 | 5.00 | 5.00 |
| Accordion (18.9 LPM) | 5% CO$_2$/Air 0.0125–0.025 | 6.13E−06 | 2.50 | 2.50 |
| Accordion (6.8 LPM) | 5% CO$_2$/Air 0.0125–0.025 | 6.13E−06 | 1.65 | 1.65 |
| Air Accordion (no pump) | 5% CO$_2$/Air 0.0143–0.0286 | 7.39E−06 | 0.00 | 7.36E−06 |

The Air Accordion bioreactor was also compared with land use and light path of other types of bioreactors based on published values (Table 3). The Air Accordion used less land, while having increased volume and surface area per m$^2$, than other types of bioreactors.

TABLE 3

Comparison of land use of Air Accordion and other bioreactors

| Reactor type | Volume (L) | Land use (m$^2$) | Volume/land use (L/m$^2$) | Surface area/land use | Light path (m) |
|---|---|---|---|---|---|
| Air Accordion | 35.0 | 0.120 | 291.63 | 13.81 | 0.06 |
| Accordion | 40.0 | 0.240 | 166.65 | 8.14 | 0.06 |
| Helical[a] | 75.0 | 1.131 | 66.31 | 8.83 | 0.03 |
| Flat plate[b] | 6.0 | 0.546 | 11.00 | 1.15 | 0.013 |
| Flat plate[b] | 25.0 | 0.546 | 45.82 | 1.15 | 0.052 |
| Flat plate[b] | 50.0 | 0.546 | 91.64 | 1.15 | 0.104 |
| Flat plate[c] | 14.0 | 0.546 | 25.66 | 1.15 | 0.028 |
| Horizontal tubular[d] | 140.0 | 77.5 | 1.81 | 1.42 | 0.14 |

[a]Lu et al., *J. Appl. Phycol.* 14: 331-342, 2002
[b]Hu et al., *Biotechnol. Bioeng.* 51: 51-60, 1996
[c]Hu et al., *Eur. J. Phycol.* 32: 81-86, 1997
[d]Vonshak et al., *Plant, Cell Envir.* 24: 1113-1118, 2001

Example 4

Microalgal Cell Culture in Air Accordion Bioreactor

This example describes culture of microalgae in an Air Accordion bioreactor over long time periods.

*M. subterraneus* cells were cultured in Air Accordion bioreactors made of a low-density polyethylene tubing sealed at both ends and installed in a support frame made of metal. The polyethylene tubing had a width of 0.457 m and a wall thickness of 0.253 mm. The bioreactor had a length of 2.57 m and an operational volume of 50.0 L. The support frame (3.05 m height×0.05 m depth×2.24 m width) was constructed of galvanized steel struts with galvanized steel bars as cross beams. Each bar was 1.27 cm in diameter. Bar spacing was optimized to provide the most even distribution of culture media throughout the bioreactor.

The bioreactors contained Miller-Fogg Optimized Medium (MF) and were inoculated with *M. subterraneus* that had been cultured in the laboratory. Inoculation concentration was 0.2 g $L^{-1}$. Each Air Accordion bioreactor was aerated by a gas sparger connected to the opening at the bottom of the bioreactor with 2-24% ($LL^{-1}$) $CO_2$/air at a gas flow rate of 0.02 $LL^{-1}$ $min^{-1}$ to maintain a pH of 7.0±0.2. The highest $CO_2$ concentration (24% $LL^{-1}$) was applied to maintain the pH with the highest cell density.

A greenhouse experiment was conducted in Tucson, Ariz. (32° 13' 18" N, 110° 55' 35" W) using daytime (5:30 AM to 7:30 PM) solar radiation from April 22 to July 22. The average sunlight intensity incident to the south-facing surface of the Air Accordion bioreactors ranged from 5 to 15 mol $m^{-2}$ $d^{-1}$ in photosynthetically active radiation (400-700 nm). The greenhouse temperature was maintained by means of evaporative cooling pads, and ranged from 15-32° C. Algae biomass samples were collected periodically, and optical density, pH and biomass were measured.

Figure 6:
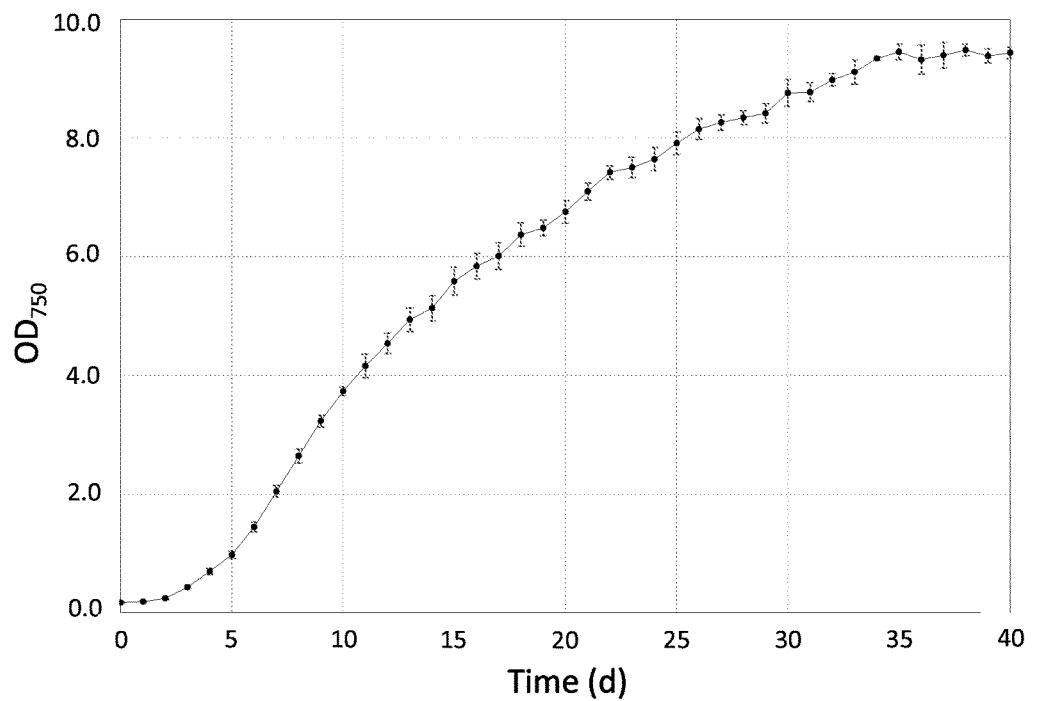
FIG. 6 is a graph showing time profile of mean $OD_{750}$ with standard deviation (n=4) of *M. subterraneus* cultured over 40 days in Air Accordion bioreactors.

The resulting growth of *M. subterraneus* in the Air Accordion bioreactor measured in optical density (OD) is shown in FIG. 6. After an initial two days of lag phase (days 0-2), the cell density increased exponentially for approximately 4 days (days 2-6) at a maximum specific growth rate (μ) of 0.45-0.61 $d^{-1}$. During days 6-10, the cell density increased linearly from 0.65 to 1.69 g $L^{-1}$ at the highest productivity of 0.25-0.35 g $L^{-1}$ $d^{-1}$. During days 10-40, the growth rate gradually declined as the cell density increased, and the cell density reached the highest concentration of 4.0-4.5 g $L^{-1}$.

Example 5

Semi-Continuous Harvesting of Microalgal Cell Culture from Air Accordion Bioreactor This example describes semi-continuous harvesting of microalgae cultured in an Air Accordion bioreactor.

*M. subterraneus* cells were cultured in Air Accordion bioreactors constructed as described in Example 4. The bioreactors contained Miller-Fogg Optimized Medium (MF) and were inoculated with *M. subterraneus* that had been cultured in the laboratory. Inoculation concentration was 0.2 g $L^{-1}$. Each Air Accordion bioreactor was aerated by a gas sparger connected to the opening at the bottom of the bioreactor with 2-24% ($LL^{-1}$) $CO_2$/air at a gas flow rate of 0.02 $LL^{-1}$$min^{-1}$ to maintain a pH of 7.0±0.2.

A greenhouse experiment was conducted in Tucson, Ariz. (32° 13' 18" N, 110° 55' 35" W) using daytime (6:00 AM to 6:00 PM) solar radiation from September 16 to November 21. The average sunlight intensity incident to the south-facing surface of the Air Accordion bioreactors ranged from 4 to 19 mol $m^{-2}$ $d^{-1}$ in photosynthetically active radiation (400-700 nm). The greenhouse temperature was maintained by means of evaporative cooling pads, and ranged from 17-41° C. About 60% of the total volume of cell culture, which was equivalent to 30 L of cell culture from each bioreactor, was harvested through a harvesting port connected to the opening at the bottom of the bioreactor every six days for 24 days from Sep. 26, 2014 to Oct. 19, 2014. After each harvesting, each bioreactor was replenished with fresh MF to a total volume of 50 L.

Similarly, about 30% of the total volume of cell culture, which was equivalent to 15 L of cell culture from each bioreactor, was harvested through the harvesting port connected to the opening at the bottom of the bioreactor every 3 days for 33 days from Oct. 20, 2014 to Nov. 22, 2014. Samples were collected periodically, and optical density, pH and biomass were measured. After each harvesting, each bioreactor was replenished with fresh MF to a total volume of 50 L.

Figure 7:
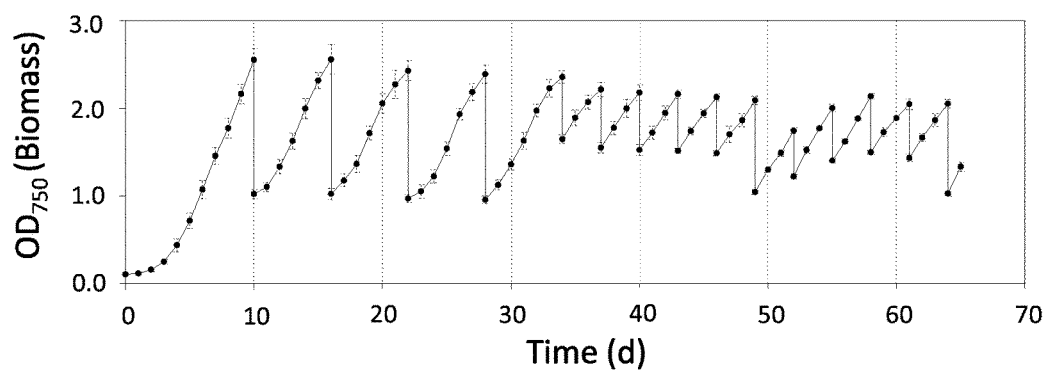
FIG. 7 is a graph showing growth of *M. subterraneous* in Air Accordion bioreactors over 65 days of experimental period with harvesting every 6 days (days 10-34) or every 3 days (days 37-65). Bars represent standard deviation with n=4.

The resulting growth of *M. subterraneus* in the Air Accordion bioreactors measured in optical density (OD) is shown in FIG. 7. Average growth rate of 0.104 g $L^{-1}$ $d^{-1}$ was observed for the total of 65 days of cultivation period. The highest growth rate observed throughout the experimental period was 0.22 g $L^{-1}$ $d^{-1}$. The total of 1.31 kg dry biomass of *M. subterraneus* was harvested over 65 days of experimental period.

In view of the many possible embodiments to which the principles of the disclosure may be applied, it should be recognized that the illustrated embodiments are only examples and should not be taken as limiting the scope of the invention. Rather, the scope of the invention is defined by the following claims. We therefore claim as our invention all that comes within the scope and spirit of these claims.

We claim:

1. A bioreactor comprising:
  (a) a container for holding fluid comprising a first sheet and a second sheet, wherein the second sheet is disposed adjacent to the first sheet and the first and second sheets are sealed along a first longitudinal edge, a second longitudinal edge, a first horizontal edge, and a second horizontal edge, and comprising at least one opening in the second horizontal edge;
  (b) a support structure comprising at least two vertical supports and at least two horizontal supports, wherein two or more portions of the container of part (a) are alternately positioned in front of and behind the at least two horizontal supports, thereby orienting the two or more portions of the container at alternating angles different from 0° relative to a vertical axis formed in the container, and wherein the angle different from 0° is between 5° and 75°; and
  (c) a gas sparger or a gas diffuser connected to the at least one opening in the second horizontal edge for providing mixing of fluid, and
  wherein the bioreactor does not comprise a liquid pump.

2. The bioreactor of claim 1, wherein the first sheet, the second sheet, or both comprise a transparent material.

3. The bioreactor of claim 1, wherein the first sheet, the second sheet, or both comprise a flexible material.

4. The bioreactor of claim 3, wherein the flexible material comprises polyethylene.

5. The bioreactor of claim 1, wherein the angle different from 0° is about 35° to 75°.

6. The bioreactor of claim 1, further comprising at least one intermediate horizontal seal between the first horizontal edge and the second horizontal edge, wherein there is at least one opening in the at least one intermediate horizontal seal.

7. The bioreactor of claim 1, wherein the sealed second horizontal edge comprises one or more angled seals.

8. The bioreactor of claim 1, further comprising at least one additional opening in the first horizontal edge, the second horizontal edge, the first longitudinal edge, or the second longitudinal edge.

9. A method of culturing cells, comprising incubating a suspension of cells in a nutrient solution in the bioreactor of claim 1 and providing mixing by sparging the culture with a gas mixture.

10. The method of claim 9, wherein the cells comprise microalgal cells, macroalgal cells, bacterial cells, fungal cells, plant cells, or mammalian cells.

11. The method of claim 10, wherein the cells are microalgal cells and the microalgal cells comprise *Chlamydomonas reinhardtii, Monodus subterraneous*, or *Botryococcus braunii*.

12. The method of claim 9, wherein the bioreactor is exposed to a light source.

13. The method of claim 12, wherein the light source is sunlight.

* * * * *